United States Patent
Gray

(10) Patent No.: US 9,149,361 B2
(45) Date of Patent: Oct. 6, 2015

(54) NON-RESORBABLE PLUGS

(71) Applicant: Presidium Biomedical LLC, Lubbock, TX (US)

(72) Inventor: Austin Gray, Fort Worth, TX (US)

(73) Assignee: PRESIDIUM BIOMEDICAL LLC, Boerne, TX (US)

( * ) Notice: Subject to any disclaimer, the term of this patent is extended or adjusted under 35 U.S.C. 154(b) by 3 days.

(21) Appl. No.: 13/648,632

(22) Filed: Oct. 10, 2012

(65) Prior Publication Data

US 2014/0100665 A1   Apr. 10, 2014

(51) Int. Cl.
*A61F 2/02* (2006.01)
*A61F 2/28* (2006.01)

(52) U.S. Cl.
CPC ....... *A61F 2/2803* (2013.01); *A61F 2002/2839* (2013.01)

(58) Field of Classification Search
CPC ....... A61F 2/12; A61F 2/3094; A61F 2/2803; A61F 2/28
USPC ..................... 623/11.11, 16.11, 23.75, 23.76; 606/151
See application file for complete search history.

(56) References Cited

U.S. PATENT DOCUMENTS

| | | | | |
|---|---|---|---|---|
| 5,141,522 | A * | 8/1992 | Landi | 523/114 |
| 5,957,690 | A | 9/1999 | Bartee et al. | |
| 7,296,998 | B2 | 11/2007 | Bartee et al. | |
| 7,604,816 | B2 | 10/2009 | Hiltner et al. | |
| 2008/0299213 | A2* | 12/2008 | Kleinsek et al. | 424/531 |
| 2009/0240267 | A1* | 9/2009 | Crawley et al. | 606/151 |
| 2010/0082072 | A1* | 4/2010 | Sybert et al. | 606/326 |
| 2011/0288506 | A1* | 11/2011 | Chowdhury | 604/290 |
| 2012/0121687 | A1* | 5/2012 | Chang et al. | 424/447 |

OTHER PUBLICATIONS

Wang et al., Mineralized Bone Allograft-Plug Socket Augmentation: Rationale and Technique, *Implant Dentistry*, 16:33-38, (2007).

* cited by examiner

*Primary Examiner* — Jason-Dennis Stewart
(74) *Attorney, Agent, or Firm* — Sterne, Kessler, Goldstein & Fox P.L.L.C.

(57) ABSTRACT

A non-resorbable wound dressing can include a plug made from polytetrafluoroethylene (PTFE). The plug can have a three-dimensional shape. The plug can be substantially cylindrical. The PTFE can have a high density and be expanded. The PTFE can be non-porous or have a porosity of less than about 0.4 microns. The PTFE can also be unsintered and unexpanded. A method of regenerating alveolar bone includes placing a PTFE plug in a cavity formed in an alveolar bone. Placing the plug in the cavity can include contacting at least a portion of a peripheral surface of the plug with the gingival tissue surrounding the cavity. The method can also include inserting a bone graft material in the cavity before placing the plug in the cavity.

15 Claims, 5 Drawing Sheets

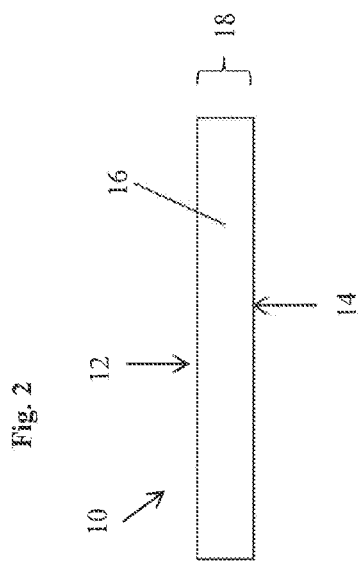
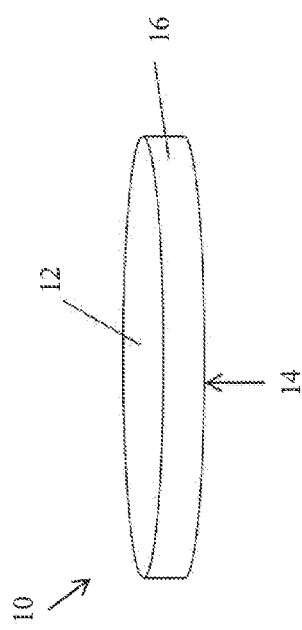
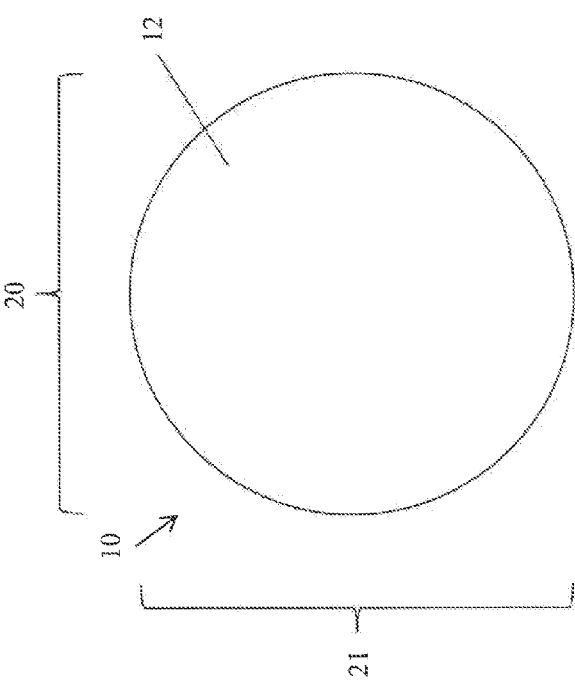

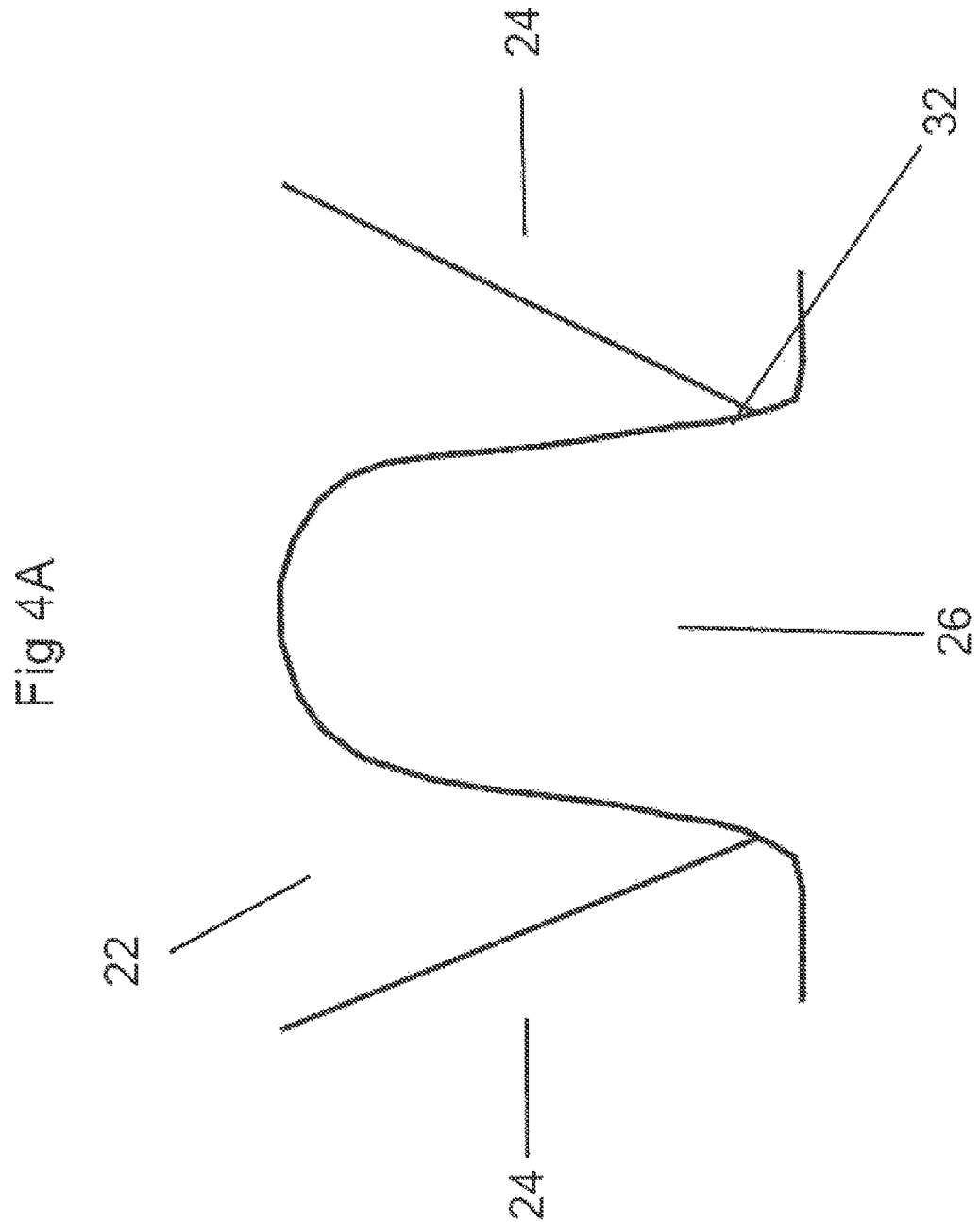

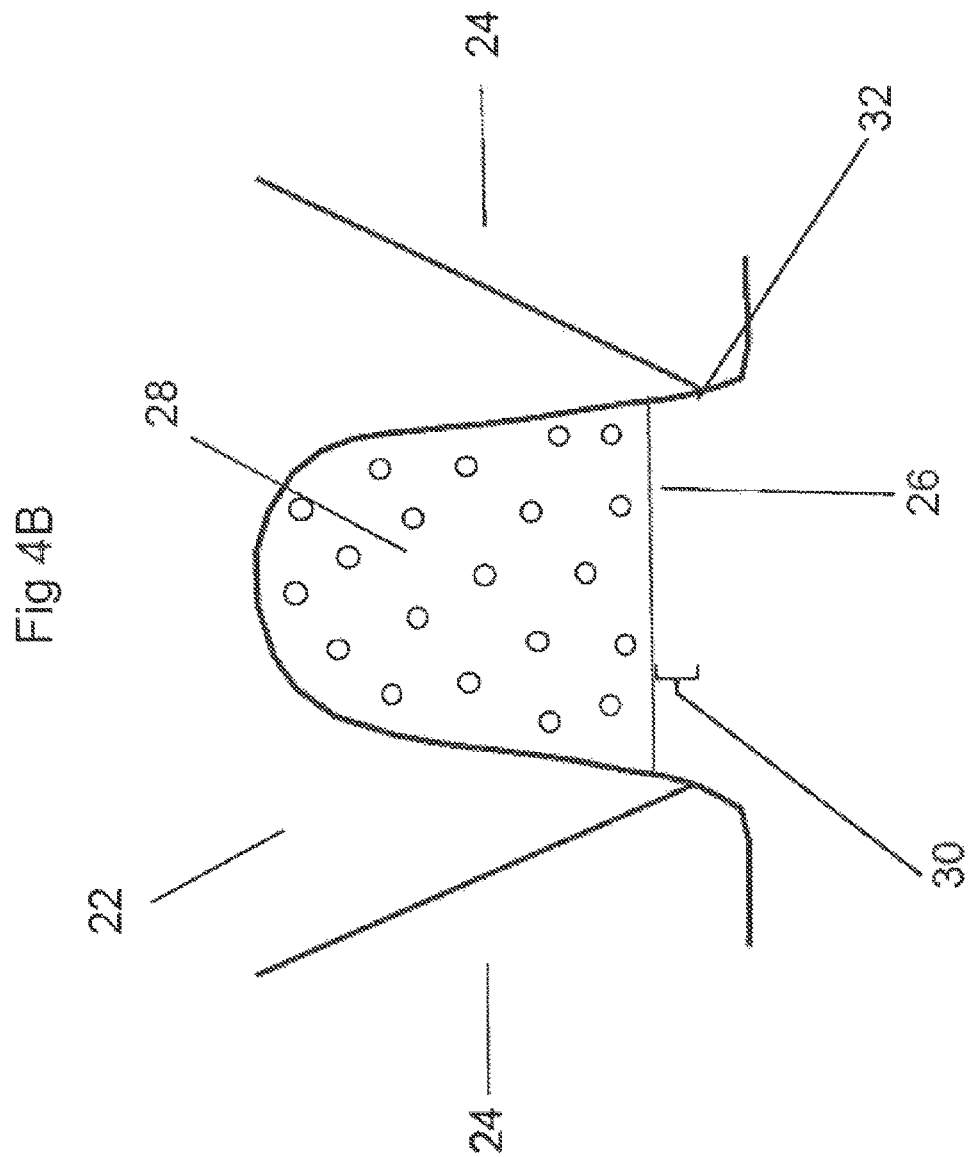

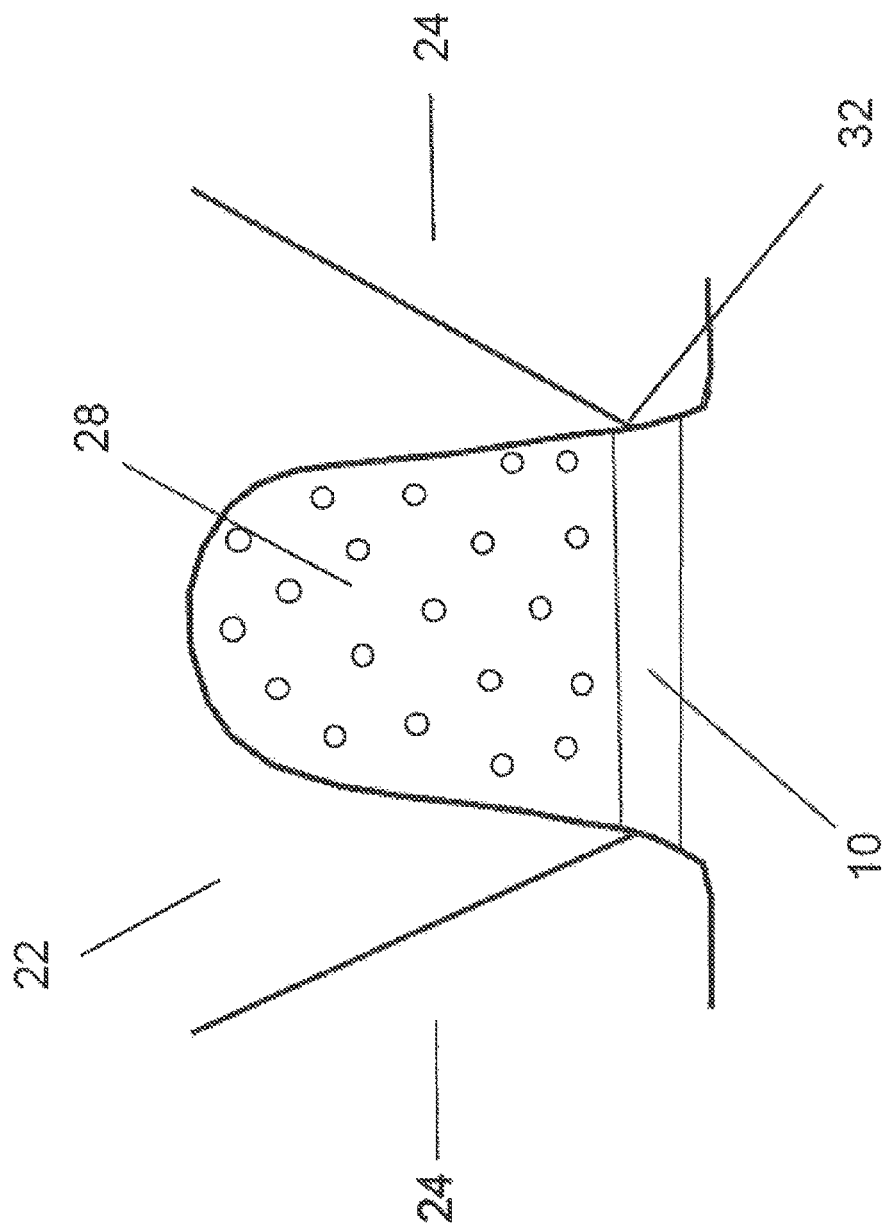

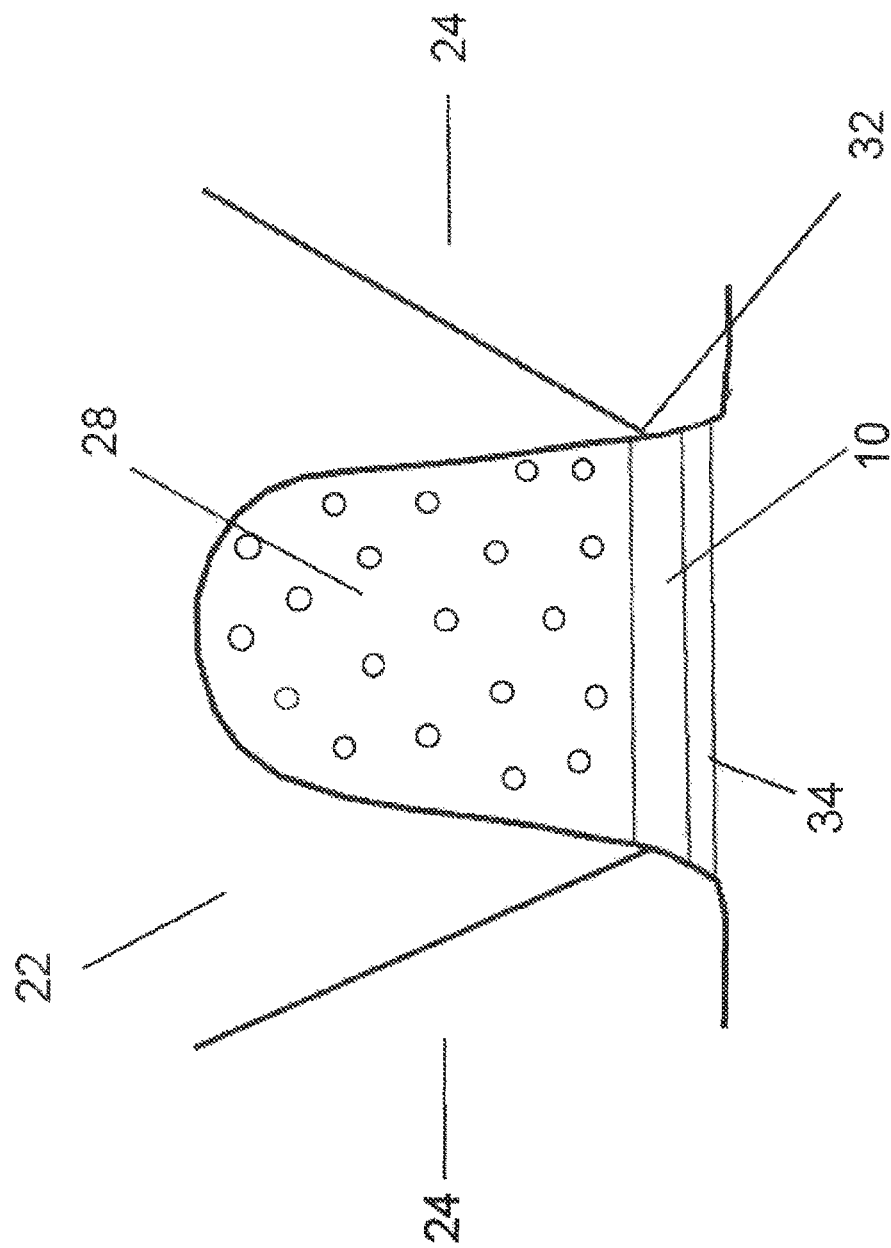

NON-RESORBABLE PLUGS

BACKGROUND

1. Field

Embodiments of the invention relate generally to non-resorbable wound dressings for treating cavities in an alveolar bone and, particularly, to three-dimensional, non-resorbable plugs.

2. Background

An alveolar bone, for example, the maxilla or the mandible, can have undesirable cavities. These cavities can occur for a variety of reasons. For example, cavities can be created by extracting a tooth or removing a cyst. Cavities can also be formed from bone loss caused by dental implants, or from a variety of other reasons. To promote bone regeneration (including ridge preservation), a bone graft material can be inserted in the cavity.

To keep the bone graft material in the cavity and, thus, maximize bone regeneration, the cavity can be substantially sealed using a barrier. For example, the cavity can be sealed with a resorbable barrier made from, for example, collagen. Resorbable barriers, however, can resorb before bone regeneration is complete. The cavity can also be sealed with a thin non-resorbable barrier such as a membranes, tape, or film. Currently, placing a thin non-resorbable planar barrier requires that buccal and lingual flaps be cut in gingival tissue and that the edges of the barrier be placed underneath the flaps, which separates the gingival tissue from the alveolar bone. This separation may retard bone regeneration. Accordingly, there is a need for a wound dressing that does not resorb before bone regeneration is substantially completed and that can reduce the separation between the gingival tissue and the bone.

BRIEF SUMMARY

In some embodiments, a non-resorbable wound dressing can include a plug made from polytetrafluoroethylene (PTFE). The plug can have a three-dimensional shape. The plug can be substantially cylindrical. The plug can have a diameter that ranges from about 4 mm to about 14 mm and a height that ranges from about 0.5 mm to about 4 mm. The PTFE can have a high density. The PTFE can be expanded or non-expanded. The PTFE can be non-porous or have a porosity of less than about 0.4 microns. The PTFE can also be unsintered or sintered.

In some embodiments, a method of regenerating alveolar bone includes placing a PTFE plug in a cavity formed in an alveolar bone. The plug can have a three-dimensional shape. Placing the plug in the cavity can include contacting at least a portion of a peripheral surface of the plug with the gingival tissue surrounding the cavity. The method can also include inserting a bone graft material in the cavity before placing the plug in the cavity. The plug can be substantially cylindrical. The plug can have a diameter that ranges from about 4 mm to about 14 mm and a height that ranges from about 0.5 mm to about 4 mm. The PTFE can have a high density. The PTFE can be expanded or non-expanded. The PTFE can be non-porous or have a porosity of less than about 0.4 microns. The PTFE can also be unsintered or sintered.

BRIEF DESCRIPTION OF THE DRAWINGS

The accompanying drawings, which are incorporated herein and form part of the specification, illustrate embodiments of the present invention and, together with the description, further serve to explain the principles of the invention and to enable a person skilled in the relevant art(s) to make and use the invention.

FIG. 1 is a side perspective view of a non-resorbable plug according to an embodiment.

FIG. 2 is a side view of the non-resorbable plug of FIG. 1.

FIG. 3 is a plan view of the non-resorbable plug of FIGS. 1-2.

FIGS. 4A-4D are cross-sectional views of an alveolar bone and surrounding gingival tissue that illustrate a method of regenerating alveolar bone according to an embodiment.

DETAILED DESCRIPTION

FIGS. 1, 2, and 3 are a perspective view, a side view, and a plan view of a plug 10 according to an embodiment. Plug 10 can be configured to at least partially seal a cavity, for example, a socket formed by extracting tooth, in an alveolar bone such as the mandible or the maxilla. Plug 10 can have a three dimensional shape—plug 10 is not a membrane, tape, or film. Barriers having a thickness less than substantially 0.25 mm are considered membranes, tape, or film.

In some embodiments, as shown in FIGS. 1-3, plug 10 can have a three-dimensional shape that includes a coronal surface 12 that faces in a direction towards the crowns of the teeth, an apical surface 14 that faces in a direction towards the root tips, and a peripheral surface 16 extending between coronal surface 12 and apical surface 14. For example, plug 10 can have a substantially cylindrical shape, for example, circular cylinder shape, an elliptical cylinder shape, or any other suitable cylindrical shape. As shown in FIGS. 1-3, plug 10 is a substantially circular cylinder in some embodiments. Coronal surface 12 and apical surface 14 are substantially circular, and peripheral surface 16 extends straight between coronal surface 12 and apical surface 14. In some embodiments, plug 10 can have a non-cylindrical shape, for example, a conical frustum shape.

Plug 10 can have a height 18. In some embodiments, height 18 can range from about 0.5 mm to about 4 mm. In some embodiments, height 18 can range from about 1 mm to about 3 mm. In some embodiments, height 18 can be about 2 mm. In some embodiments, plug 10 can have a width 20 in a buccal-lingual direction and a depth 21 in a mesial-distal direction. Width 20 and depth 21 can each range from about 4 mm to about 14 mm. In some embodiments, width 20 and depth 21 can be about 9 mm. In some embodiments, width 20 and depth 21 are the same, and in other embodiments, width 20 and depth 21 vary. For example, as shown in FIGS. 1-3, width 20 and depth 21 are the same—the diameters of substantially circular coronal surface 12 and apical surface 14. In some embodiments, coronal surface 12 and apical surface 14 are substantially planar. In some embodiments, coronal surface 12 and apical surface 14 are substantially non-planar. In some embodiments, plug 10 can be sized such that peripheral surface 16 contacts alveolar bone or the surrounding gingival tissue.

In some embodiments, plug 10 can be pre-fabricated and sized to fit within the cavity in the alveolar bone without being trimmed by a clinician. In some embodiments, plug 10 can be configured such that the size and shape of plug 10 be easily adjusted by a clinician, for example, by trimming plug 10 with scissors.

Plug 10 can be made from one or more non-resorbable material. If plug 10 is made from a non-resorbable material, plug 10 can reside in the cavity of the alveolar bone for an extended period of time without being resorbed. Being non-resorbable, plug 10 can protect a bone graft material (explained further below with reference to FIGS. 4A-4C) placed in the cavity in the alveolar bone for a period of time longer than traditional collagen plugs, which can help promote bone regeneration and reduce the risk of infection.

In some embodiments, the non-resorbable material can be a hydrophilic or hydrophobic polymeric material. In some embodiments, the polymeric material is hydrophilic because hydrophilic polymers are believed to promote tissue wetting and, therefore, healing of the surrounding tissue. In some embodiments, the polymeric material is generally non-porous. But in other embodiments, low porosity polymers can be used. The polymeric material suitable for use in various embodiments is generally puncture resistant such that polymer plug 10 is not negatively impacted by the patient's chewing of solid food.

In some embodiments, the polymeric material is a fluoropolymer. For example, the polymeric material can be polytetrafluoroethylene (PTFE) or derivatives of PTFE. In some embodiments, the polymeric material can be polypropylene. In some embodiments, the polymeric material is a polymer having similar biocompatibility, physical and chemical properties to PTFE. For example, the polymeric material can be any other suitable fluoropolymer such as polyvinylfluoride, polyvinylidene fluoride, polychlorotrifluoroethylene, perfluoroalkoxy polymer, perfluoroalkoxy polymer, fluorinated ethylenepropylene, polyethylenetetrafluoroethylene, polyethylenechlorotrifluoroethylene, perfluorinated elastomer, chlorotrifluoroethylenevinylidene fluoride, or perfluoropolyether.

In embodiments in which the polymeric material is a fluoropolymer, the fluoropolymer can have a high density—a density greater than about 1.0 gm/cc. The high density fluoropolymer can have a density that ranges from about 1.0 gm/cc to about 2.5 gm/cc. In some embodiments, the high density fluoropolymer can have a density in a range from about 1.2 gm/cc to about 2.3 gm/cc. For example, in embodiments in which the polymeric material is PTFE, the PTFE can have a high density—a density greater than about 1.0 gm/cc. The high density PTFE can have a density that ranges from about 1.0 gm/cc to about 2.5 gm/cc. In some embodiments, the high density PTFE can have a density in a range from about 1.2 gm/cc to about 2.3 gm/cc.

In some embodiments, the PTFE can be sintered and expanded PTFE. In some embodiments, the PTFE can be sintered and unexpanded. In some embodiments, the PTFE can be unsintered and unexpanded. In some embodiments, the PTFE can be unsintered and expanded.

In some embodiments, the PTFE can be non-porous. In some embodiments, the PTFE can have low porosity. For example, the PTFE can have porosity less than about 0.4 microns. In some embodiments, the PTFE can have a porosity less than about 0.3 microns. In some embodiments in which PTFE is either non-porous or has a low porosity, plug 10 can help prevent bacteria from reaching the bone and the bone graft material in the cavity of the alveolar bone, which can reduce the risk of infection. In some embodiments, the PTFE can have a porosity more than about 0.4 microns. For example, the PTFE can have a porosity of about 3 microns, about 4 microns, or more than about 4 microns.

In some embodiments, plug 10 can be coated or embedded with a microbiocide. For example, coronal surface 12 can be coated with the microbiocide. In some embodiments, the microbiocide is an anti-biotic. In some embodiments, the microbiocide is an active silver-based biocide.

In some embodiments, plug 10 can be substantially rigid relative to a membrane composed of the same material. For example, plug 10 can be sufficiently rigid to firmly press against the alveolar bone when placed. This pressure helps seal the cavity in the alveolar bone and helps prevent plug 10 from being dislodged after placement, for example, by a patient's chewing. In some embodiments, plug 10 can be at least about four times stiffer than a membrane made of the same material and having the same width 20 or depth 21 as plug 10. In some embodiments, plug 10 is about eight times, about ten times, about 15 times, or more than about 15 times stiffer than a membrane made of the same material. For example, a plug 10 with a rectangular cross-section having a height 18 of about 0.5 mm and a width 20 of about 9 mm would have an area moment of inertia of about 0.09375 mm$^4$ (I=(9 mm*0.5 mm$^3$)/12=0.09375 mm$^4$). And a membrane with a rectangular cross-section having a height 18 of about 0.25 mm and width of about 9 mm would have an area moment of inertia of about 0.01172 mm$^4$ (I=(9 mm*0.25 mm$^3$)/12=0.01172 mm$^4$). Accordingly, the area moment of inertia of plug 10 would be about eight times larger than the area moment of inertia of the membrane, which would result in an about eight-fold increase in stiffness of plug 10 relative to the membrane. Increasing the height 18 of plug 10 from about 0.5 mm would further increase the stiffness of plug 10 relative to the membrane having a height of 0.25 mm or less.

In some embodiments, plug 10 can comprise a fluoropolymer, for example, PTFE, encasing a non-resorbable core.

FIGS. 4A-4D are cross-sectional views of an alveolar bone 22 and gingival tissue 24 that illustrate a method of using plug 10 to regenerate alveolar bone according to an embodiment. As shown in FIG. 4A, alveolar bone 22 has a cavity 26. In some embodiments, cavity 26 can be formed by a dental surgery, for example, cyst removal or tooth extraction. In some embodiments, cavity 26 is formed natural bone loss caused by dental implants, trauma, bone atrophy, or any other manner that may create a cavity in alveolar bone 22.

A bone graft material 28 is inserted into cavity 26 as shown in FIG. 4B. Bone graft material 28 can be any suitable bone graft material, for example, any suitable autograft, allograft, xenograft, or alloplast bone graft material. In some embodiments, cavity 26 can be filled with bone graft material 28 until a distance 30 between the coronal boundary of bone graft material 28 and a crest 32 of alveolar bone 22 is in a range from about 1 mm to about 2 mm. In some embodiments, bone graft material 28 is filled in cavity 26 until distance 30 is greater than or equal to about 0.1 mm.

In some embodiments, cavity 26 is filled with bone graft material 28 so that distance 30 is less than height 18 of plug 10. In some embodiments, distance 30 is about 50 percent of height 18 of plug 10. In some embodiments distance 30 is more than about 50 percent, for example, about 75 percent, or less than about 50 percent, for example, about 25 percent, of height 18 of plug 10. In such embodiments, if plug 10 is placed flush against bone graft material 28, gingival tissue 24 directly contacts a coronal portion of peripheral surface 16 of plug 10, and alveolar bone 22 directly contacts an apical portion of peripheral surface 16 of plug 10. In other words, a coronal portion of plug 10 projects above crest 32 of alveolar bone 22.

In some embodiments, cavity 26 is filled with bone graft material 28 so that distance 30 is greater than height 18 of plug 10. In such embodiments, if plug 10 is placed flush against bone graft material 28, alveolar bone 22 directly contacts the entire peripheral surface 16 of plug 10, and coronal surface 12 of plug 10 is below crest 32 of alveolar bone 22. In other words, plug 10 is recessed below crest 32 of alveolar bone 22.

In some embodiments, cavity 26 is filled with bone graft material 28 so that distance 30 is about equal to height 18 of plug 10. In such embodiments, if plug 10 is placed flush against bone graft material 28, alveolar bone 22 directly contacts the entire peripheral surface 16 of plug 10, but plug 10 neither projects above nor is recessed below crest 32 of alveolar bone 22.

After bone graft material 28 is inserted into cavity 26, plug 10 is placed in the remaining unfilled portion of cavity 26 as shown in FIG. 4C. In some embodiments, plug 10 is trimmed to snugly fit within cavity 26 such that alveolar bone 22 and/or gingival tissue 24 directly contacts peripheral surface 16 of plug 10. For example, a clinician can trim plug 10 such that diameter 20 of plug 10 is about equal to a diameter of cavity 26. In some embodiments, a clinician can also trim plug 10 such that the shape of coronal and apical surfaces 12 and 14 more closely corresponds to the shape of cavity 26. As shown in FIGS. 4C and 4D, an apical portion of peripheral surface 16 of plug 10 directly contacts alveolar bone 22, and a coronal portion of peripheral surface 16 of plug 10 directly contacts gingival tissue 24 in some embodiments.

Plug 10 can be placed in cavity 26 without having to cut flaps in gingival tissue 24, and plug 10 can be placed in cavity 26 without separating gingival tissue 24 from the buccal or lingual surfaces of alveolar bone 22, which may help promote bone regeneration. Without being limited by theory, separating gingival tissue 24 from buccal surface of alveolar bone 22 disrupts blood flow or supply to alveolar bone 22. This separation may also negatively affect bone regeneration by removing tissue that supplies nutrients and biological factors that promote bone regeneration. This separation may also negatively affect the recruitment of white blood cells, which may make the site more susceptible to infection.

In some embodiments, as shown in FIG. 4D, plug 10 can be secured within cavity 26 by one or more sutures 34 or any other suitable securement technique. Plug 10 can be removed from cavity 26 after an extended period of time, for example, about 3 to about 6 weeks after placement. During this time, bone regeneration occurs under plug 10. In some embodiments, plug 10 is removed between about 21 days and about 28 days after placement. If sutures 34 are used to secure plug 10 in cavity 26, sutures 34 are severed, and plug 10 is removed.

Surprisingly, the bone regeneration achieved after using a non-resorbable plug such as a PTFE plug as described above, has been comparable to, if not better than, the bone regeneration achieved by using a resorbable plug such as a collagen plug.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A non-resorbable wound dressing, comprising:
   a plug comprising a fluoropolymer,
   wherein the plug has a three-dimensional shape configured to fit within a cavity of an alveolar bone such that the plug contacts the alveolar bone or surrounding gingival tissue, and wherein the plug has a porosity less than about 0.4 microns or is non-porous.

2. The non-resorbable wound dressing of claim 1, wherein the three-dimensional shape is a substantially cylindrical shape having a coronal surface, an apical surface, and a peripheral surface extending between the coronal surface and the apical surface.

3. The non-resorbable wound dressing of claim 2, wherein the plug has a height ranging from about 0.5 mm to about 4 mm.

4. The non-resorbable wound dressing of claim 2, wherein the coronal surface and the apical surface are substantially circular.

5. The non-resorbable wound dressing of claim 4, wherein the coronal surface and the apical surface each have a diameter ranging from about 4 mm to about 14 mm.

6. The non-resorbable wound dressing of claim 1, wherein the fluoropolymer is polytetrafluoroethylene (PTFE).

7. The non-resorbable wound dressing of claim 6, wherein the PTFE has a high density.

8. The non-resorbable wound dressing of claim 7, wherein the high density is in a range from about 1.0 gm/cc to about 2.5 gm/cc.

9. The non-resorbable wound dressing of claim 7, wherein the PTFE is expanded.

10. The non-resorbable wound dressing of claim 7, wherein the PTFE is unsintered and unexpanded.

11. The non-resorbable wound dressing of claim 1, wherein the plug has a rigidity such that the plug firmly presses against the alveolar bone or surrounding gingival tissue when place within the cavity.

12. The non-resorbable wound dressing of claim 11, wherein pressure between the plug and the alveolar bone or surrounding gingival seals the cavity of the alveolar bone.

13. The non-resorbable wound dressing of claim 1, wherein the plug is configured to be removed from the cavity of the alveolar bone between 3 to 6 weeks after placement.

14. A non-resorbable wound dressing, comprising:
   a plug comprising a fluoropolymer,
   wherein the plug has a three-dimensional shape configured to fit within a cavity of an alveolar bone,
   wherein the plug the plug has a porosity less than about 0.4 microns or is non-porous, and
   wherein the plug is configured to be removed from the cavity of the alveolar bone between 3 to 6 weeks after placement.

15. The non-resorbable wound dressing of claim 14, wherein the plug is configured to press against the alveolar bone or surrounding gingival tissue when placed within the cavity such that the cavity of the alveolar bone is sealed.

* * * * *